(12) United States Patent
Olsvik et al.

(10) Patent No.: US 7,168,488 B2
(45) Date of Patent: Jan. 30, 2007

(54) METHOD AND PLANT OR INCREASING OIL RECOVERY BY GAS INJECTION

(75) Inventors: Ola Olsvik, Hundhamaren (NO); Erling Rytter, Trondheim (NO); Jostein Sogge, Stjørdal (NO); Rune Kvale, Stavanger (NO); Sjur Haugen, Lommedalen (NO); Jan Grøntvedt, Stavanger (NO)

(73) Assignee: Statoil ASA, Stavanger (NO)

( * ) Notice: Subject to any disclaimer, the term of this patent is extended or adjusted under 35 U.S.C. 154(b) by 171 days.

(21) Appl. No.: 10/487,785

(22) PCT Filed: Aug. 30, 2002

(86) PCT No.: PCT/NO02/00305

§ 371 (c)(1),
(2), (4) Date: Aug. 5, 2004

(87) PCT Pub. No.: WO03/018959

PCT Pub. Date: Mar. 6, 2003

(65) Prior Publication Data

US 2004/0256116 A1 Dec. 23, 2004

(30) Foreign Application Priority Data

Aug. 31, 2001 (WO) .................... PCT/NO01/00356

(51) Int. Cl.
*E21B 43/18* (2006.01)
*E21B 43/34* (2006.01)

(52) U.S. Cl. .................... 166/266; 166/90.1; 166/267; 166/268; 166/305.1

(58) Field of Classification Search ............ 166/75.12, 166/90.1, 266, 267, 268, 272.1, 303, 305.1, 166/401, 402
See application file for complete search history.

(56) References Cited

U.S. PATENT DOCUMENTS

| 4,223,728 | A | * | 9/1980 | Pegg | 166/266 |
| 4,501,445 | A | * | 2/1985 | Gregoli | 299/2 |
| 4,761,167 | A | * | 8/1988 | Nicholas et al. | 62/626 |
| 5,097,903 | A | * | 3/1992 | Wilensky | 166/266 |
| 5,133,406 | A | * | 7/1992 | Puri | 166/266 |
| 5,749,422 | A | * | 5/1998 | Michael | 175/71 |
| 5,769,165 | A | * | 6/1998 | Bross et al. | 166/266 |
| 5,862,869 | A | * | 1/1999 | Michael | 175/71 |
| 6,016,868 | A | * | 1/2000 | Gregoli et al. | 166/261 |
| 6,054,496 | A | * | 4/2000 | Crane et al. | 518/702 |
| 6,505,683 | B2 | * | 1/2003 | Minkkinen et al. | 166/266 |
| 6,595,291 | B1 | * | 7/2003 | Lia et al. | 166/305.1 |

* cited by examiner

*Primary Examiner*—George Suchfield
(74) *Attorney, Agent, or Firm*—Kirkpatrick & Lockhart Nicholson Graham LLP

(57) ABSTRACT

A method and a plant for simultaneous production of a gas for injection into an oil field and production of methanol, dimethyl ether and/or other oxygenated hydrocarbons or production of higher hydrocarbons from natural gas is disclosed. An air separation unit (ATR) for production of pure nitrogen for injection and pure oxygen for production of synthesis gas ("syngas") by authermal reformation of a natural gas is an essential part of the method and plant.

21 Claims, 4 Drawing Sheets

METHOD AND PLANT OR INCREASING OIL RECOVERY BY GAS INJECTION

CROSS REFERENCE TO RELATED APPLICATIONS

This application is based on International Application No. PCT/NO02/00305, filed 30 Aug. 2002, having an International Publication Number of WO 03/018959 A1 and an International Publication Date of 6 Mar. 2003, which is based on International Application No. PCT/NO01/00356, filed 31 Aug. 2001.

THE FIELD OF THE INVENTION

The present invention regards the use of natural gas in the development of industry and oil fields. In particular, the invention regards a method and a plant for integrated production of synthesis gas and gas for injection into an oil reservoir.

THE BACKGROUND OF THE INVENTION

The reinjection of various gases into an oil reservoir in order to enhance the oil recovery from the reservoir, and to stabilize it, has long been known and used. Gases such as $CO_2$, $N_2$ and natural gas will reduce the surface tension between gas and oil, and thus contribute to both increased recovery and stabilization of the reservoir.

Natural gas as such may be injected into fields where the gas does not have a net value that exceeds the excess profits of increasing the oil recovery in the field Cleaning waste gas from the combustion on the production installation can provide $CO_2$ for injection into oil reservoirs. In addition it has been suggested that $CO_2$ cleaned from the waste gas from gas power plants be reinjected by laying a pipeline from a gas power plant to the production installation for hydrocarbons.

$N_2$ may be produced together with $O_2$ in a so-called air separation unit (ASU). In an oil field, such an air separation unit will normally produce $N_2$ with a purity of >99.9% and oxygen-enriched air. There is little or no need for this oxygen-enriched air on the oil field, and all or most of this is therefore released.

Separation of air into an "oxygen-depleted stream" and an "oxygen-enriched stream" is described in U.S. Pat. Nos. 5,388,645 and 6,119,778. The oxygen-depleted stream is used for injection into a "solid carbonaceous formation" for improved recovery of methane and at least a part of the oxygen-enriched stream is used for reaction with a reactant stream containing at least one oxidizable reactant. Examples of processes are steel making operations, production of non-ferrous metals, chemical oxidation processes and production of synthesis gas for Fischer-Tropsch synthesis of higher from natural gas. The oxygen-depleted stream has a nitrogen to oxygen volume ratio of 9:1 to 99:1. A too high ratio may lead to the formation of an explosive gas. An oxygen-depleted gas, e.g. nitrogen, for injection into an oil field to enhance the production preferably includes less than 0.1% oxygen.

No other integration between the processes using the oxygen-depleted and oxygen-enriched streams is mentioned in U.S. Pat. Nos. 5,388,645 or 6,119,778.

Natural gas may also be used as feed for a number of processes such as the production of methanol, dimethyl ether or other oxygenated hydrocarbons, and/or synthetic fuel/propellant. This can take place in accordance with known processes such as described in PCT/NO00/00404.

Plants for production of methanol and other oxygenated hydrocarbons and/or synthetic fuel often require $O_2$ produced in an air separation unit in order to produce synthesis gas ("syngas"). Syngas is a mixture of CO, $CO_2$, $H_2$ and water vapor and some non-reacted natural gas. The syngas is used in various synthesis reactions, such as for the production of methanol and other oxygenated hydrocarbons, heavier hydrocarbons and ammonia. The oxygen produced in an air separation unit in such a plant is typically >95% pure oxygen, while the nitrogen will be relatively impure nitrogen that is not suitable for other applications, and is therefore released to the atmosphere.

A process for preparation of higher hydrocarbons and for enhancing the production of crude oil from an underground formation is described in Canadian Patent No. 1,250,863. The off-gas from the synthesis plant is oxidized into mainly $CO_2$ and $H_2O$ before it is injected into the underground formation. Preferably, the presence of nitrogen is avoided by using oxygen from an air separation unit for all oxygen-demanding processes.

A SUMMARY OF THE INVENTION

According to the present invention, there is provided a method for increasing oil recovery from an oil reservoir in which method gas is injected into the reservoir, comprising the steps of:

separating of air into an oxygen-rich fraction and a nitrogen-rich fraction;

providing a natural gas stream and leading the natural gas stream and at least a part of the oxygen-rich fraction to a reformer for conversion to synthesis gas mainly comprising $H_2$, CO and $CO_2$ in addition to lower amounts of non-converted methane, water vapor and oxygen;

synthesizing methanol or other oxygenated hydrocarbons or higher hydrocarbons from the synthesis gas in a synthesis unit;

withdrawing a waste gas from the synthesis unit; and injecting the nitrogen-rich fraction and at least a part of the waste gas into the oil reservoir to increase the oil recovery from the reservoir.

According to a preferred embodiment, the method further comprises separation of the waste gas from the synthesis unit into a $CO_2$-rich fraction and a fraction low in $CO_2$ and using the $CO_2$-rich fraction for injection into the oil reservoir.

Preferably the waste gas from the synthesis unit is combusted with oxygen prior to separation into a $CO_2$-rich fraction and a fraction low in $CO_2$.

The waste gas from the synthesis loop is preferably combusted at an elevated pressure, preferably at a pressure of from 2 to 100 bar, more preferably from 20 to 40 bar.

According to a second embodiment of the present invention, the waste gas from the synthesis unit is separated into a $CO_2$-rich fraction and a fraction low in $CO_2$, and that the fraction low in $CO_2$ is then combusted in a gas turbine or a furnace.

The fraction low in $CO_2$ that exits the synthesis loop may in a preferred embodiment be split into a hydrogen-rich fraction and a fraction low in hydrogen, where the hydrogen-rich fraction is sent to a process that requires the addition of hydrogen, and the fraction low in hydrogen is combusted.

According to an embodiment it is preferred that the waste gas from the synthesis loop is combusted in a furnace or a turbine, and that the exhaust gas from the furnace or turbine is separated into a $CO_2$-rich fraction that is injected into the oil reservoir, and a fraction low in $CO_2$.

Furthermore, it is preferred that the exhaust gas from the furnace or turbine goes through secondary combustion in a catalytic secondary combustion chamber before being separated into a $CO_2$-rich fraction and a fraction low in $CO_2$.

It is also preferred that natural gas is added to the furnace or turbine.

According to another embodiment it is preferred that a part of the synthesis gas bypasses the synthesis unit.

Also provided is a plant for providing gas for downhole injection for pressure support in an oil reservoir for recovery of hydrocarbons and production of methanol, dimethyl ether and/or other oxygenated hydrocarbons or for production of higher hydrocarbons from natural gas, comprising:

an air separation unit for production of an oxygen-rich fraction for supply to processes that require oxygen, and a nitrogen fraction for injection;

a reformer for conversion of a mixture of natural gas, water and oxygen from the air separation unit into a synthesis gas comprising mainly $H_2$, CO, $CO_2$ and small amounts of methane;

a synthesis unit for conversion of the synthesis gas for synthesis of methanol or other oxygenated hydrocarbons, or for synthesis of synthetic fuel;

means for injecting gas into the reservoir;

means for transferring nitrogen from the air separation unit to the means for injecting gas; and means for transferring at least a part of a waste gas from the synthesis unit to the means for injecting gas.

According to a preferred embodiment the means for transferring waste gas from the synthesis unit comprises one or more separation units for separating the waste gas into a $CO_2$-rich fraction that is led to the unit for injection for pressure support, and a fraction low in $CO_2$.

It is preferred that the plant further comprises a furnace or a gas turbine for combustion of the waste gas from the synthesis unit and a line for leading oxygen for the combustion from the air separation unit to the furnace or gas turbine.

According to a preferred embodiment the plant further comprises means of separating the waste gas from the synthesis unit into a $CO_2$-rich fraction and a fraction low in $CO_2$, and a gas turbine or a furnace for combustion of the fraction low in $CO_2$.

The plant preferably comprises means of splitting the low $CO_2$ fraction of the waste gas from the synthesis unit into a hydrogen rich fraction and a fraction low in hydrogen.

According to a preferred embodiment the plant further comprises a furnace or a gas turbine for combustion of the waste gas from the synthesis unit and means of separating the exhaust gas from the furnace or turbine into a $CO_2$-rich fraction that is led to the unit for injection for pressure support, and a fraction low in $CO_2$.

It is preferred that the plant comprises a catalytic secondary combustion chamber for secondary combustion of the exhaust gas from the furnace or turbine prior to it being separated into a $CO_2$-rich fraction and a fraction low in $CO_2$.

Preferably, the plant further comprises a bypass line for leading some of the added natural gas past the reformer and the synthesis unit, to the furnace or turbine.

It is preferred that the plant further comprises a bypass line for leading some of the synthesis gas past the synthesis unit.

By combining a plant for production of high-purity nitrogen with the production of oxygen, the co-producing air separation unit only becomes 10–20% more expensive than an air separation unit that only produces high-purity nitrogen for injection into oil fields. This allows significant cost savings, both for production of synthesis products such as methanol and synthetic fuel, and for oil field injection.

A BRIEF DESCRIPTION OF THE FIGURES

DETAILED DESCRIPTION OF THE INVENTION

Figure 1:
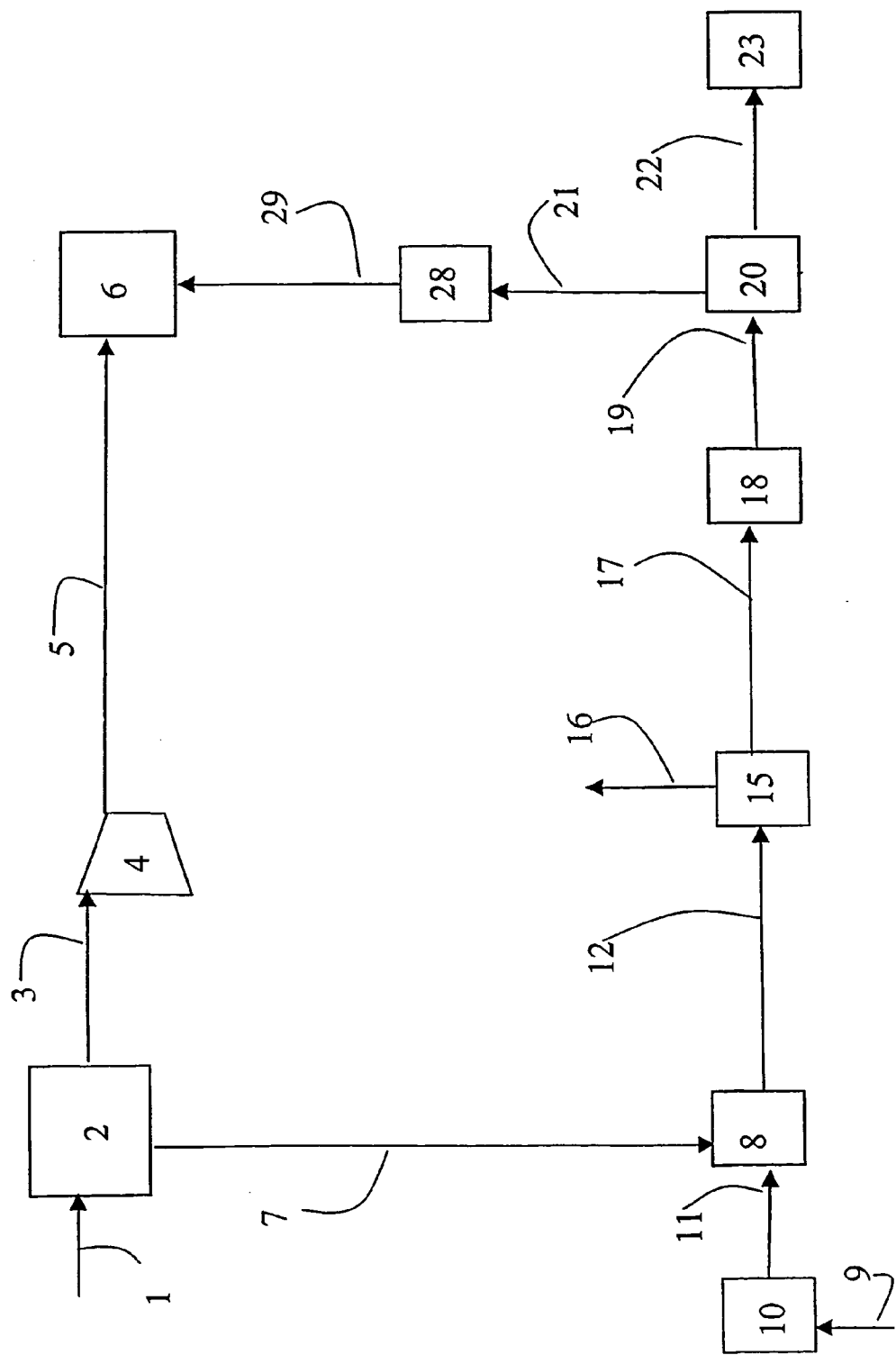
FIG. 1 shows a schematic diagram of an embodiment of the present invention.

FIG. 1 is a schematic diagram showing the principal features of a preferred embodiment of the present invention. Air is drawn in through an air intake 1 to an air separation unit 2, where it is separated into the main components nitrogen and oxygen. The air separation unit differs from traditional air separation units used for production of oxygen to reformers or for production of nitrogen for injection into an oil well, in that it produces nitrogen and oxygen with a high purity. The produced nitrogen typically has a purity of >99.9%, while the oxygen typically has a purity of 98–99.5%.

The nitrogen is passed through line 3 to a compressor 4 where it is compressed to the desired pressure, e.g. of the order of 50–400 bar. From the compressor 4, the compressed nitrogen stream is passed through a line 5 to a plant 6 for injection of gas into a field, a so-called EOR unit ("Enhanced Oil Recovery").

The oxygen is passed through a line 7 to a synthesis gas production unit, a so-called reformer 8.

Natural gas is fed to the plant through a gas inlet 9. Prior to the natural gas being sent into line 11 to the reformer for production of synthesis gas, it is treated in a pre-treatment unit 10 in which sulphur compounds are removed in a conventional manner. The steam is then saturated into the gas and/or added directly to the gas. The saturation may take place by means of a so-called saturator. Often, the gas is also treated in a so-called pre-reformer in order to convert all heavier hydrocarbons (C2+) before the gas is sent into the reformer 8.

In the reformer, the following are the main chemical reactions to take place during the production of synthesis gas:

1. $CH_4 + H_2O = CO + 3H_2$, steam reforming
2. $CH_4 + 3/2O_2 = CO + 2H_2O$, partial oxidation
3. $CO + H_2O = CO_2 + H_2$, shift reaction Reaction 1 in the reforming reactor is highly endothermic, and the heat required for the reaction may either be added through external heating, such as in a steam reformer, or through a combination with internal partial oxidation according to reaction 2, such as in an autothermal reformer.

In a steam reformer (SR), natural gas (NG) is converted in a tubular reactor at a high temperature and relatively low pressure. A conventional steam reformer consists of a large number of reactor tubes in a combustion chamber. Conventional steam reformers are operated in a pressure range from approximately 15 to 40 bar. The outlet temperature for such a reformer can get up to 950° C. The heat required to drive the reaction is added by means of external heating in the combustion chamber in which the reformer tubes are installed.

The reformer may be top, bottom or terrace fired. The heat can also be transferred to the reaction by means of convective heat as in a heat exchanger reactor. The ratio between steam and carbon in the feed gas is from 1.6 to 4. The composition of the synthesis gas may as an example be expressed in stoichiometric numbers $(SN=(H_2-CO_2)/(CO_2+CO))$. The stoichiometric number for the product stream from the steam reformer is approximately 3 when the natural gas contains pure methane. A typical synthesis gas from a conventional steam reformer contains approximately 3 volume % methane.

In an autothermal reformer (ATR), the synthesis gas production mainly takes place through reactions 1 and 2, such that the heat required for reaction 1 is generated internally via reaction 2. In an ATR, natural gas (methane) is led into a combustion chamber together with an oxygen-containing gas such as air. The temperature of the combustion chamber can get up to over 2000° C. After the combustion, the reactions are brought to an equilibrium across a catalyst before the gases leave the reformer at a temperature of approximately 1000° C. The stoichiometric number, SN, for the product stream from an ATR is approximately 1.6–1.8. The pressure may typically be around 30–40 bar, but a significantly higher pressure has also been proposed, such as in the range 40–120 bar. The steam/carbon ratio may vary with the intended application, from 0.2 to 2.5.

An alternative autothermal reformer makes use of a concept called partial oxidation (POX). Such a reformer does not contain any catalyst for accelerating the reactions, and will therefore generally have a higher outlet temperature than an ATR.

Reformation of natural gas may also take place through combined reforming (CR), where the reformer section consists of a SR and an ATR. A combination of SR and ATR allows the composition exiting the reformer section to be adjusted by regulating the admission to the two reformers. SR will in CR be operated under somewhat milder conditions than in the case of normal SR, i.e. at a somewhat lower temperature. This results in a slightly higher methane slippage in the outlet gas from the reformer. This methane content is converted in the subsequent ATR. The ratio between steam and carbon in the gas feed will, for such a reformer, lie in the range 1.2 to 2.4, with a stoichiometric number, SN, of around 2 or slightly on the high side of 2.

The desired composition of the synthesis gas will depend on the process for which it is to form the raw material. The optimum stoichiometric number for methanol synthesis is around 2.05, while the desired stoichiometric number for production of synthetic fuel often lies in the range 1.6 to 1.9, as a higher stoichiometric number gives a greater yield of lighter hydrocarbons than that which is desirable.

After reforming, the synthesis gas is cooled by being heat exchanged with water to give steam. Upon further cooling, water from the synthesis gas is condensed before being sent on via a line 12 to a synthesis unit 15.

The synthesis unit 15 may for instance be a synthesis unit for production of synthetic fuel (heavier hydrocarbons), comprising a so-called Fischer-Tropsch reactor (F-T reactor), or a synthesis unit for production of oxygenated hydrocarbons such as methanol and dimethyl ether.

When the synthesis unit 15 is a synthesis unit for production of synthetic fuel, the reaction may be described using the following reaction equation:

$$nCO+2nH_2=[-CH_2-]_n+nH_2O$$

The reaction is highly exothermic. The Fischer-Tropsch synthesis is well known and is described e.g. in PCT/NO00/00404.

When the synthesis unit 15 is a synthesis unit for production of methanol, this synthesis takes place according to the following two reaction equations:

$$CO+2H_2=CH_3OH$$

$$CO_2+3H_2=CH_3OH+H_2O$$

These exothermal reactions normally take place in a tubular reactor at a pressure of 60–100 bar and a temperature of 230–270 degrees C. The methanol synthesis is also well known and is described e.g. in PCT/NO00/00450.

Both of the above synthesis units comprise a number of components per se, and both processes normally include internal recycling of non-reacted synthesis gas in order to increase the carbon efficiency of the process.

The product from the synthesis unit 15 is extracted through a product outlet 16 for further treatment. Non-reacted synthesis gas and inert gas that collects in the loop can be removed from the synthesis unit 15 through line 17. This gas will in the following description be denoted the waste gas from the synthesis unit. The amount and composition of the waste gas from the synthesis unit depends on the released methane in the synthesis gas from the reformer section, as well as selected process parameters in the synthesis unit For the methanol synthesis, the volume of waste gas from the synthesis unit may be small. In this case, this gas may be released or combusted prior to being released in order to avoid emissions of hydrocarbons and CO.

If $CO_2$ is required for injection into the oil well in addition to nitrogen, or if environmental conditions require the emission of $CO_2$ from the plant to be reduced, the waste gas from the synthesis unit may alternatively be passed further to a CO shift converter 18 in which non-converted CO is converted according to the following reaction equation:

$$CO+H_2O \rightarrow CO_2+H_2$$

in order to make it easier to separate out the carbon contents of the gas.

From the CO shift converter, the gas may if required be led through a line 19 to a $CO_2$ recovery unit 20 in which $CO_2$ is separated from the other constituents of the gas. $CO_2$ may be separated out by means of an absorption process, e.g. by means of an amine, a cryogenic process or possibly by means of membranes. From the recovery unit 20, $CO_2$ is led via a line 21, a compressor 28 and further via a line 29 to EOR unit 6.

The gas that was separated from $CO_2$ in the recovery unit 20, and which mainly consists of $H_2$, $CH_4$ and inert gases, is passed further through a line 22 to other uses in a unit 23.

The unit 23 may be a furnace in which the gas is combusted under the addition of air, oxygen or oxygen-enriched air and provides heat for a heat-requiring process. Alternatively, the gas may be burnt in a gas turbine alone or as additional heating. Alternatively, hydrogen may be separated from the gas before it is burnt or alternatively released. Hydrogen may here be used for hydrogen-requiring processes such as e.g. upgrading of oil by sweetening (removal of sulphur), for saturation of unsaturated hydrocarbons and hydrocracking or for use in fuel cells.

If there is a great need for $CO_2$ for injection, the use of a so-called "once through" reactor in the synthesis unit 15 may also be envisaged, i.e. a reactor without any recycling.

Figure 2:
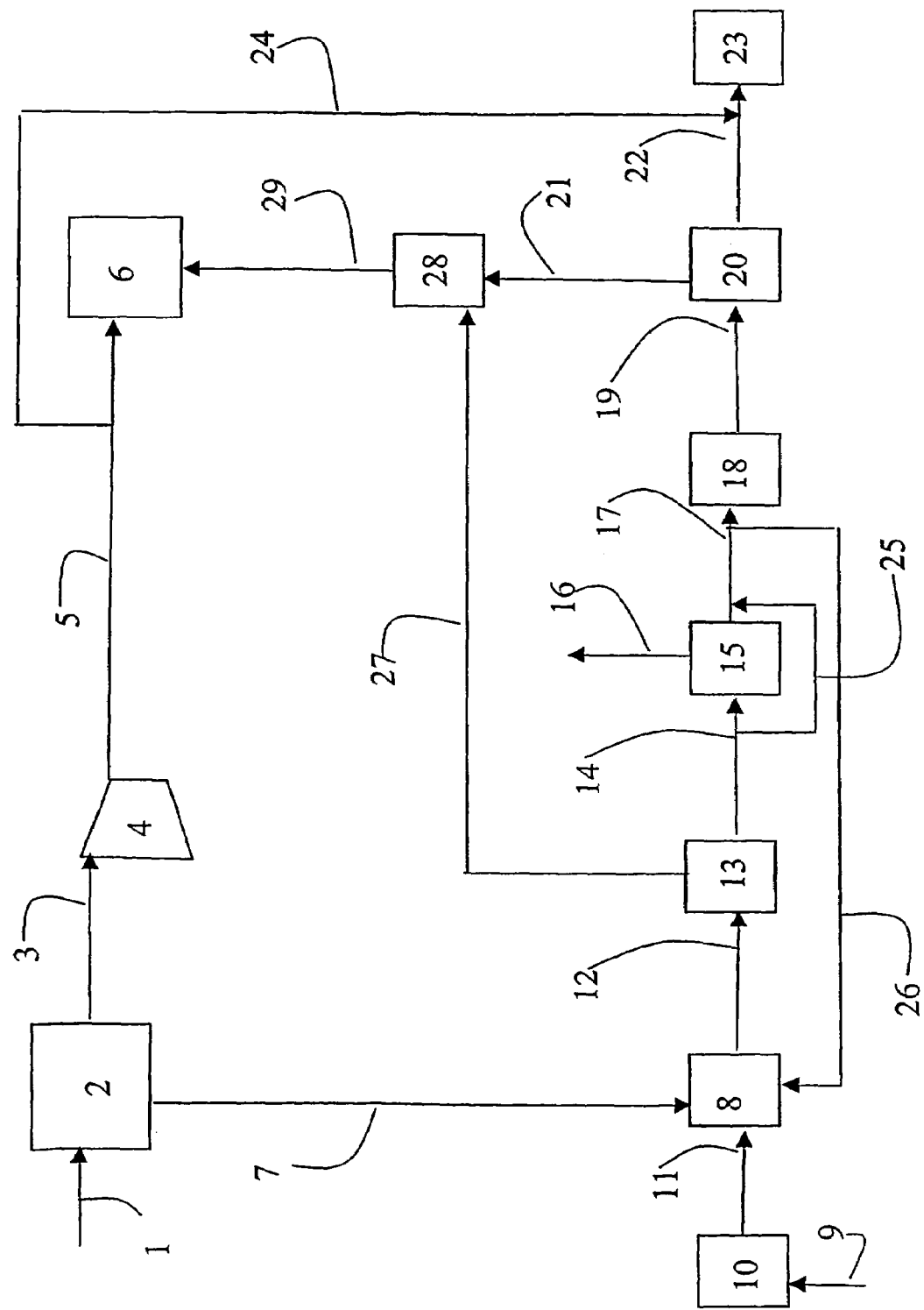
FIG. 2 shows a schematic diagram of alternative options for the present invention.

FIG. 2 shows alternative and optional embodiments of a plant according to the present invention. The figure is based on the same principal units as FIG. 1, but some optional, and in some cases preferred, additional units besides bypass lines and feedback lines, have been added in order to ensure the highest possible conversion or in order to adjust the composition of the gas.

A $CO_2$ recovery unit 13 may be interposed between the reformer 8 and the synthesis unit 15. By so doing, a desired amount of $CO_2$ can be removed from the synthesis gas and passed through a line 27 to the compressor 28, where it is brought together with $CO_2$ from line 21. This can be used as a means of changing the stoichiometric number of the synthesis gas so as to give it an optimum composition.

When the synthesis unit 15 is a synthesis unit for production of synthetic fuel, synfuel, it may also be desirable to recycle non-reacted synthesis gas from line 17 to the reformer 8 via line 26. By recycling via line 26, the $H_2/CO$ ratio of the synthesis gas may be adjusted to the desired value, i.e. around 2.0 or just below 2.0, and the CO yield and thereby also synthetic fuel yield may be increased by the high content of $CO_2$ in the recycling gas suppressing further conversion of CO to $CO_2$ through the shift reaction in the autothermal reformer. Here, it should be noted that $CO_2$ is to be considered an inert gas in the F-T synthesis.

If the reformer 8 produces more synthesis gas than can be converted in the synthesis unit 15, some of the synthesis gas may be led from a line 14 running between the $CO_2$ recovery unit 13 and the synthesis unit 15, and around the synthesis unit 15 in a bypass line 25. This may also be desirable if there is a wish to produce more heat or power in a furnace or gas turbine 23.

In certain cases it may also be desirable to remove a volume of nitrogen from line 5 out into a line 24 and bring this together with the gas in line 22, which is led to a turbine in unit 23 in order to control the combustion and generation of heat in this.

The units 13 and 20 for separating $CO_2$ from the remainder of the gas are known units. By the reformer 8 being supplied with pure oxygen instead of air, the volume of gas to be treated becomes considerably smaller. The separation in the units 13, 20 may take place in a known manner by means of semi-permeable membranes or by absorption with subsequent desorption, e.g. in a solution of alcohol amines.

The air separation unit 2 is preferably a plant based on cryogenic distillation, however it is also possible to use plants based on pressure swing adsorption and/or membranes.

Figure 3:
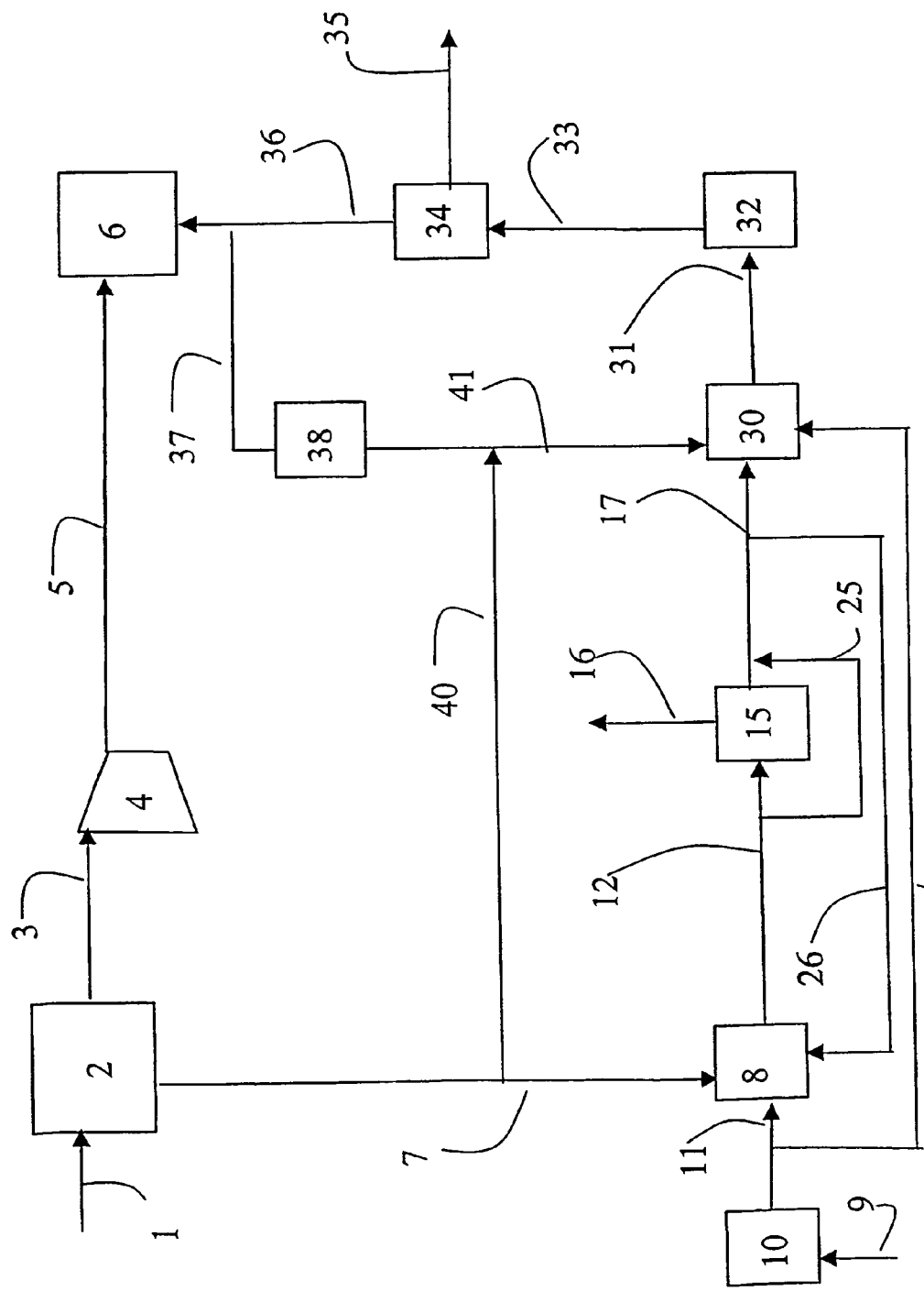
FIG. 3 shows an alternative embodiment of the present invention.

FIG. 3 shows a third embodiment in which non-converted synthesis gas from the synthesis unit 15 is combusted with pure oxygen in a furnace or gas turbine 30. Units having the same reference numbers as in FIGS. 1 or 2 indicate similar units with a similar functionality.

Oxygen is passed from line 7 through a line 40 and mixed with $CO_2$ in a line 41, from where it passes into furnace or gas turbine 30. The waste gas from the furnace or gas turbine 30 goes via a line 31 to a catalytic secondary combustion chamber 32 in which the remaining fuel in the form of CO, $H_2$ or non-combusted hydrocarbon is converted catalytically. The products of combustion from the secondary combustion chamber 32 are passed via a line 33 to a condensation unit 34, where water is condensed out and led out through a line 35, while $CO_2$ is passed to the EOR unit 6 via a line 36.

$CO_2$ may be led from line 36 via a line 37 to a compressor 38. For this configuration, some compressed $CO_2$ must be recycled via line 41 to the furnace or gas turbine 30 in order to maintain the combustion temperature in this below a given maximum temperature.

If the requirement for heat and/or power is great, or there is a requirement for large volumes of $CO_2$, natural gas from line 11 may be led via a line 42 directly to the furnace or gas turbine 30.

Preferably, the combustion in the furnace or gas turbine 30 takes place at an elevated pressure, such as from 2 to 100 bar, more preferably from 20 to 40 bar. Having the combustion take place with pressurized oxygen facilitates the separation of $CO_2$ in the following condensation unit 34.

The great advantage of the present method and plant is that they allow simple and energy efficient operation of the combined plant. The present method also allows a more efficient and financially justifiable method of removing $CO_2$ from the waste gas from a methanol plant or plant for production of synthetic fuel, for injection, so as to allow the emission of $CO_2$ to be eliminated or at least reduced considerably.

Those skilled in the art will appreciate that there may be units in the above figures for adjusting the pressure of the gases, such as compressors or reducing valves that are not shown, but which are necessary in order to match the pressures of the various units and to ensure that the streams flow in the right direction. Moreover, there may be units for heating or cooling, or heat exchangers that are not shown here, the function of which is to optimise the energy efficiency of the plant.

EXAMPLE

Calculations have been carried out for a plant according to FIG. 1 for production of methanol, which in addition comprises a bypass line that leads some of the synthesis gas in line 12 past the synthesis unit 15 and on to line 17.

The air separation unit can deliver 38 400 MTPD $N_2$ and 6400 MUD $O_2$. This air separation unit requires approximately 115 MW of power, which is delivered in the form of high pressure steam from the synthesis gas section.

The nitrogen is extracted at 3 bar and 0 degrees C. The gas is compressed to 220 bar for reinjection. Compression requires approximately 304 MW.

The oxygen can be fed to an autothermal reformer for production of synthesis gas from natural gas. The process operates with a steam/carbon ratio of 0.6. The temperature and pressure at the outlet from the ATR is 1030 degrees Celsius and 45 bar respectively. See Table 1 for the natural gas composition. Note, all compositions are given on a dry basis, i.e. without water.

TABLE 1

Composition of feeds to synthesis gas section

| | Natural gas Mole % | Oxygen Mole % |
|---|---|---|
| $CH_4$ | 83.7 | |
| $C_2H_6$ | 5.2 | |
| $C_{3+}$ | 3.2 | |
| $CO_2$ | 5.2 | |
| $N_2$ + Ar | 2.7 | 1.0 |
| $O_2$ | 0.0 | 99.0 |
| $H_2O$ | 0.0 | |
| Sum | 100 | |
| Total [$Sm^3/hr$] | 367 000 | 190 850 |

Synthesis gas is compressed to 90 bar and mixed with recycled hydrogen in order to 20 achieve a stochiometric number of 2.56 prior to the methanol synthesis. 10 000 MFPD of methanol is produced.

TABLE 2

Gas compositions

| | ATR outlet Mole % | MeOH reactor inlet Mole % | Purge gas Mole % | CO shift converted purge gas Mole % | $CO_2$ purified purge gas Mole % |
|---|---|---|---|---|---|
| $H_2$ | 62.9 | 65.9 | 27.3 | 38.7 | 52.6 |
| CO | 28.5 | 16.3 | 24.2 | 3.1 | 4.2 |
| $CO_2$ | 4.8 | 6.7 | 12.7 | 26.8 | 0.4 |
| $CH_4$ | 2.5 | 7.2 | 23.7 | 21.6 | 29.4 |
| $N_2$ + Ar | 1.3 | 3.9 | 12.1 | 9.8 | 13.4 |
| Sum | 100 | 100 | 100 | 100 | 100 |
| Total [$Sm^3$/hr] | 1 093 000 | 3 488 000 | 113 000 | 136 000 | 100 000 |

The waste gas from the synthesis unit, the purge gas, is sent to CO shift conversion. 35 t/h of steam is added in order to convert 85% of CO to $CO_2$ in a low temperature shift converter (200 degrees Celsius).

99% of the $CO_2$ in converted purge gas (equivalent to 1700 MTPD $CO_2$) is recovered in an MDEA process. Due to a high concentration of $CO_2$ in the natural gas feed, this example includes $CO_2$ removal prior to ATR (equivalent to 800 MTPD $CO_2$), so that the total amount of recovered $CO_2$ is 2500 MD. Recovered $CO_2$ is compressed to 220 bar, and may if so desired be mixed with nitrogen prior to injection into the reservoir. $CO_2$ will then constitute around 6.2 weight % of the total injection gas. $CO_2$ constitutes a relatively small share of the total injectable gas. The cleaning of this may end up being so costly that it will only be done if required by the authorities.

The remaining purge gas is used in fired heaters for superheating of steam in power production and preheating of natural gas feeds.

TABLE 3

Power balance

| Power balance | [MW] |
|---|---|
| ASU incl. $O_2$ compression | 115 |
| $CO_2$ recovery | 3 |
| $CO_2$ compression | 11 |
| $N_2$ compression | 304 |
| Synthesis/methanol section | −155 |
| Total | 278 |

Here, the requirement for added power is approximately 280 MW.

Model for Evaluation of Economical Value

The benefit of using the nitrogen byproduct produced by the air-separation unit (ASU) of a GTL plant, for enhanced oil recovery (EOR), may be evaluated by analyzing the potential impact on the gas price of the GTL plant. The natural gas price is without any doubt a major factor determining the profitability of such a plant, and a credit will be achieved for selling nitrogen.

Nitrogen and methane has roughly the same properties in EOR operations, essentially as pressure support. In the outset, we may therefore assume that the value of the neat nitrogen is equivalent to the gas price. We then will have:

P: Natural gas price in the area of the GTL facility.

$P^{Net}(GTL)=aP-bcP$ (Area gas price−credit for nitrogen sale) where the coefficients are:

a) A factor reflecting the impact on the general gas price in the area due to the integration. If P is the gas price with independent GTL and EOR operations, integration will significantly decrease the total demand for gas, and may therefore put pressure on the price, i.e., a <1.

b) The amount of nitrogen produced for a given amount (moles or energy) of natural gas used by the GTL plant. For a facility with an ATR (autothermal reformer) unit, a typical oxygen consumption O2/NG is 0.63, giving N2/NG=2.34. This number will vary with the technical concept, gas composition etc., but is used in the following to illustrate the impact of the EOR-GTL integration.

c) A factor presumably <1 taking into account that all the nitrogen produced may not be sold, e.g. due to overall well management, maintenance etc. Further, operational risks regarding continuous nitrogen delivery may put pressure on the nitrogen price.

The equation above may be modified further:

$P^{Net}(GTL)=aP-bcP+I+dS$ where

I: The investment needed to implement the integration. This will essentially be some additional costs in the ASU to secure production of nitrogen at a required purity, (additional) compression of the nitrogen, piping from the GTL to the EOR plant and possibly credit for energy integration. All these factors are recalculated by accepted methods to a cost (e.g. net present value) per amount natural gas used in the GTL plant.

S: Total savings (per amount natural gas) in the GTL gas price by the integration. This means that $S=P-(aP-bcP+I)$ d: The part of the savings that is passed onto the EOR operator for participating in the integration project, usually 0<d<0.5. The factor d might be a complicated function and there might also be overlap between the impact of factors c and d.

Illustrating Example

Figure 4:
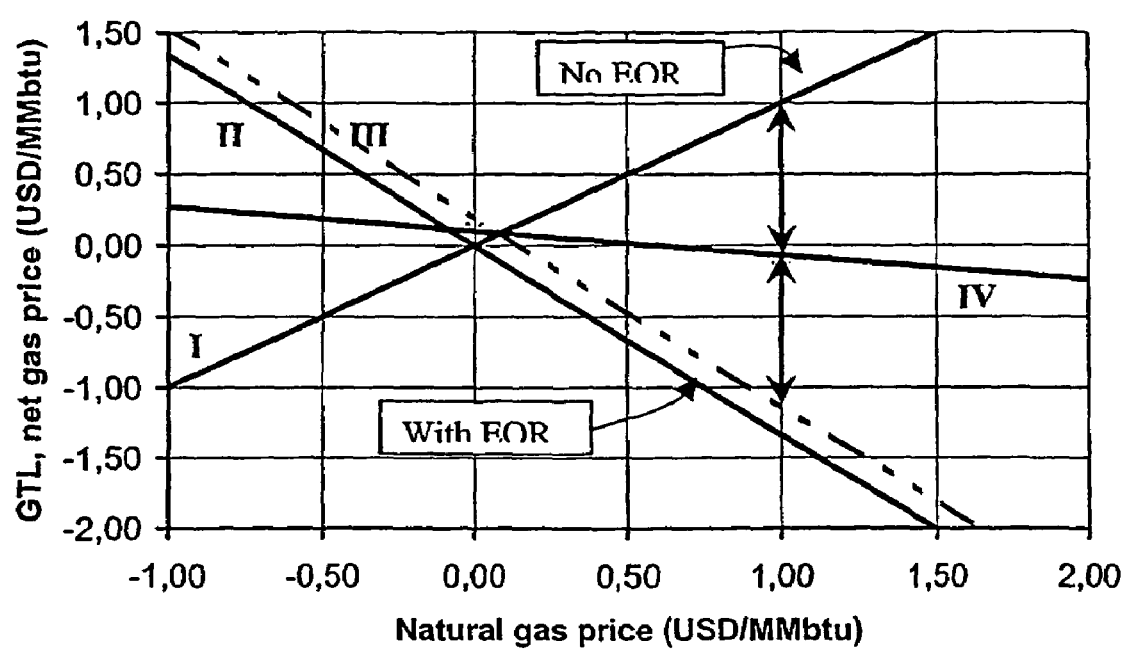
FIG. 4 is an illustration of the economical impact of the integrated process according to the present invention.

Assuming that a=1, b=2.34, c=1, I=0.2 (here 0.2 USD/MMbtu) and d=0.5, the impact of the integration is illustrated in FIG. 4. The lines are:

$P^{Net}(GTL)=aP=P$ (No EOR)  I:

$P^{Net}(GTL)=aP-bcP=-1.34P$  II:

$P^{Net}(GTL)=aP-bcP+I=-1.34P+0.2$  III:

$P^{Net}(GTL)=aP-bcP+I+dS=-0.17P+0.1$  IV:

A few interesting things can be observed in the figure. First, line II indicates that there is a huge potential if a relevant EOR case can be found. Line III shows that such an integration project will be robust against significant added investments. Further, line IV illustrates the point that even by passing half of the savings in the gas price over to the EOR operator, the net GTL gas price actually will be lower for a high gas price in the area. At a nominal gas price of 1 USD/MMbtu, the vertical arrows indicate that the added value for both plants is 1.085 USD/MMbtu of GTL feed gas.

There will be no incentive for a GTL/EOR integration at a nominal gas price below the crossing of lines I, III and IV, i.e. when I=bcP, or when the added investment equals the potential for nitrogen sales. This occurs for a gas price of I/bc, or 0.085 USD/MMbtu in this example. The only case where a negative gas price will encourage integration is when the investment of integration is negative, a situation that may occur when there is no alternative use for the excess energy from the GTL plant.

We claim:

1. A method for increasing oil recovery from an oil reservoir in which method gas is injected into the reservoir, comprising:
   separating air into an oxygen-rich fraction and a nitrogen-rich fraction;
   providing a natural gas stream and leading the natural gas stream and at least a part of the oxygen-rich fraction to a reformer for conversion to synthesis gas mainly comprising $H_2$, CO, and $CO_2$ in addition to lower amounts of non-converted methane, water vapor, and oxygen;
   synthesizing methanol or other oxygenated hydrocarbons or higher hydrocarbons from the synthesis gas in a synthesis unit;
   withdrawing a waste gas from the synthesis unit; and
   injecting the nitrogen-rich fraction and at least a part of the waste gas into the oil reservoir to increase the oil recovery from the reservoir.

2. The method according to claim 1, further comprising separating the waste gas from the synthesis unit into a $CO_2$-rich fraction and a fraction low in $CO_2$ and using the $CO_2$-rich fraction for injection into the oil reservoir.

3. The method according to claim 2, wherein the waste gas from the synthesis unit is combusted with oxygen prior to separation into a $CO_2$-rich fraction and a fraction low in $CO_2$.

4. The method according to claim 3, wherein the waste gas is combusted at an elevated pressure of from 2 to 100 bar.

5. The method according to claim 4, wherein the waste gas is combusted at an elevated pressure of from 20 to 40 bar.

6. The method according to claim 3, wherein the waste gas is combusted in a furnace or a turbine, and that the exhaust gas from the furnace or turbine is separated into a $CO_2$-rich fraction that is injected into the oil reservoir, and a fraction low in $CO_2$.

7. The method according to claim 6, wherein the exhaust gas from the furnace or turbine goes through secondary combustion in a catalytic secondary combustion chamber before being separated into a $CO_2$-rich fraction and a fraction low in $CO_2$.

8. The method according to claim 6, wherein natural gas is added to the furnace or turbine.

9. The method according to claim 2, wherein the fraction low in $CO_2$ is split into a hydrogen-rich fraction and a fraction low in hydrogen, where the hydrogen-rich fraction is sent to a process that requires the addition of hydrogen, and the fraction low in hydrogen is combusted.

10. The method according to claim 1, wherein the waste gas from the synthesis unit is separated into a $CO_2$-rich fraction and a fraction low in $CO_2$, and that the fraction low in $CO_2$ is then combusted in a gas turbine or a furnace.

11. The method according to claim 1, wherein a part of the synthesis gas bypasses the synthesis unit.

12. A plant for providing gas for downhole injection for pressure support in an oil reservoir for recovery of hydrocarbons and production of methanol, dimethyl ether and/or other oxygenated hydrocarbons or for production of higher hydrocarbons from natural gas, comprising:
   an air separation unit for production of an oxygen-rich fraction for supply to processes that require oxygen, and a nitrogen fraction for injection;
   a reformer for conversion of a mixture of natural gas, water, and oxygen from the air separation unit into a synthesis gas comprising mainly $H_2$, CO, $CO_2$ and small amounts of methane;
   a synthesis unit for conversion of the synthesis gas for synthesis of methanol or other oxygenated hydrocarbons, or for synthesis of synthetic fuel;
   means for injecting gas into the reservoir;
   means for transferring nitrogen from the air separation unit to the means for injecting gas; and
   means for transferring at least a part of a waste gas from the synthesis unit to the means for injecting gas.

13. The plant according to claim 12, wherein the means for transferring waste gas from the synthesis unit comprises one or more separation units for separating the waste gas into a $CO_2$-rich fraction that is led to a unit for injection for pressure support, and a fraction low in $CO_2$.

14. The plant according to claim 13, further comprising means for separating the waste gas from the synthesis unit into a $CO_2$-rich fraction and a fraction low in $CO_2$, and a gas turbine or a furnace for combustion of the fraction low in $CO_2$.

15. The plant according to claim 13, further comprising means of splitting the low $CO_2$ fraction of the waste gas from the synthesis unit into a hydrogen rich fraction and a fraction low in hydrogen.

16. The plant according to claim 12, further comprising a furnace or a gas turbine for combustion of the waste gas from the synthesis unit and a line for leading oxygen for the combustion from the air separation unit to the furnace or gas turbine.

17. A plant according to claim 16, further comprising means for separating the exhaust gas from the furnace or turbine into a $CO_2$-rich fraction that is led to a unit for injection for pressure support, and a fraction low in $CO_2$.

18. The plant according to claim 17, further comprising a catalytic secondary combustion chamber for secondary combustion of the exhaust gas from the furnace or turbine prior to it being separated into a $CO_2$-rich fraction and a fraction low in $CO_2$.

19. The plant according to claim 17, further comprising a bypass line for leading at least a portion of an added natural gas past the reformer and the synthesis unit to the furnace or turbine.

20. The plant according to claim 12, further comprising a bypass line for leading at least a portion of the synthesis gas past the synthesis unit.

21. A plant for providing gas for downhole injection for pressure support in an oil reservoir for recovery of hydrocarbons and production of methanol, dimethyl ether and/or other oxygenated hydrocarbons or for production of higher hydrocarbons from natural gas, comprising:
   an air separation unit configured to produce an oxygen-rich fraction;
   a reformer configured to convert a mixture of natural gas and oxygen from the air separation unit into a synthesis gas comprising mainly $H_2$, CO, $CO_2$ and lower amounts of methane;
   a synthesis unit configured to convert the synthesis gas for synthesis of methanol or other oxygenated hydrocarbons, or for synthesis of synthetic fuel;
   a first line in communication with the synthesis unit and configured to withdraw a waste gas therefrom for transfer to a unit for injection; and
   a second line in communication with the air separation unit and configured to transfer nitrogen from the air separation unit to the unit for injection.

* * * * *